United States Patent [19]
Goode et al.

[11] Patent Number: 5,350,363
[45] Date of Patent: Sep. 27, 1994

[54] ENHANCED SHEATH VALVE

[75] Inventors: Roberta D. Goode, Miami; Lawrence A. Weinstein, Davie, both of Fla.

[73] Assignee: Cordis Corporation, Miami Lakes, Fla.

[21] Appl. No.: 77,242

[22] Filed: Jun. 14, 1993

[51] Int. Cl.⁵ ............................................. A61M 5/178
[52] U.S. Cl. .................................... 604/167; 604/256
[58] Field of Search ............... 604/164, 167, 256, 283; 137/849; 251/149.1

[56] References Cited

U.S. PATENT DOCUMENTS

| | | | |
|---|---|---|---|
| 4,424,833 | 1/1984 | Spector et al. | 137/849 |
| 4,610,674 | 9/1986 | Suzuki et al. | 604/167 |
| 4,626,245 | 12/1986 | Weinstein | 137/849 |
| 4,798,594 | 1/1989 | Hillstead | 604/167 |
| 4,895,565 | 1/1990 | Hillstead | 604/167 |
| 4,929,235 | 5/1990 | Merry et al. | 137/849 |
| 4,932,633 | 6/1990 | Johnson et al. | 604/256 |
| 5,102,395 | 4/1992 | Cheer et al. | 604/167 |
| 5,167,637 | 12/1992 | Okada et al. | 604/167 |
| 5,176,652 | 1/1993 | Littrell | 604/167 |
| 5,242,413 | 9/1993 | Heiliger | 604/167 |

FOREIGN PATENT DOCUMENTS 0344907 12/1989 European Pat. Off. ............ 604/167

OTHER PUBLICATIONS 2 sheets drawings entitled Hemaquet Plus Gasket.

Primary Examiner—John G. Weiss
Attorney, Agent, or Firm—Gerstman, Ellis & McMillin, Ltd.

[57] ABSTRACT

A valve comprises an elastomeric partition member having first and second opposed faces, the valve being adapted for securement in a housing. Typically, one or both of the faces define a recess of substantially rectangular cross section to reduce the central thickness of the partition member, the recesses being wider than they are deep. The elastomeric partition is typically made of an elastomer having an elongation of 900 to 1500 percent, a tensile strength of at least 11.5 megapascals, a Shore 'A' durometer of preferably 45 to 70, and a tear strength of at least 150, as determined by tests described herein. Significant improvements are achieved by slit partition valves which utilize the elastomeric partition member of this invention.

30 Claims, 1 Drawing Sheet

ENHANCED SHEATH VALVE

BACKGROUND OF THE INVENTION

Slit elastomer medical instrument valves are disclosed in Hillstead U.S. Pat. No. 4,895,565 and in numerous other patents. Such valves may be placed on the proximal end of a catheter sheath introducer, for example, to permit the introduction of a catheter or guidewire into the arterial system of a patient while preventing back bleeding through the proximal end of the catheter sheath introducer, even when a catheter or guidewire is present.

Such slit partition valves vary in their effectiveness. Particularly, such valves vary in the effectiveness of seal as a catheter or guidewire passes through the slit. Also, the various valves vary in the amount of frictional resistance they exhibit to the advancement of a catheter or the like through the valve.

Additionally, prior art valves have been subject to tearing of the elastomer material as a catheter is advanced through it. Coronary catheters may require advancement on the order of one hundred centimeters through the valve, with several catheters being sequentially inserted and withdrawn, which represents a substantial degree of friction, stress, and wear upon the slit elastomeric partition. Particularly, tearing can be instituted at the ends of the slit. In prior art designs, the slit ends may have to be reinforced to prevent such tearing.

In accordance with this invention, a new elastomeric partition member is provided for use in a valve such as a medical hemostasis valve. Significant improvements in both sealing of a catheter or the like passing through the partition valve, and reduction of friction encountered by such a catheter, are provided. Additionally, tearing of the partition during a catheter advancement or retraction step is a greatly reduced problem in the partition valves of this invention, even without reinforcement of the slit ends.

DESCRIPTION OF THE INVENTION

In accordance with this invention, a valve of a catheter comprises an elastomeric partition member having a first face and a second, opposed face which is adapted for securement in a housing. At least one, and preferably both, of the faces define a recess of substantially rectangular cross section, which has the effect of reducing the central thickness of the partition member. The rectangular cross sections each have a first side parallel to the plane of the partition member, which first side is of greater length than the sides of the rectangular cross section adjacent thereto. In other words, the recess or recesses present are preferably wider than they are deep. Also, as is conventional, a slit is provided, extending between the first and second faces within the recess or recesses.

It is preferred for the type of slit used to be that which is used in Hillstead U.S. Patent Nos. 4,798,594 and 4,895,565, which are incorporated by reference herein. Briefly, the slit comprises intersecting radii at the beginning of the slit on one surface, which rotate through the thickness of the partition to define similar, intersecting radii on the other surface, but at an angle to the first intersecting radii.

Preferably, the intersecting radii are lines extending generally radially from an origin, with the lines occupying a circular area having a diameter of at least 0,125 inch and no more than about 0.2 inch, typically no more than about 0.150 inch. Also, the central thickness of the partition member, i.e., that part of the partition member which is within the one or more recesses, is preferably of a thickness of 0.030 or 0.035 to 0,055 inch.

The rectangular cross section of the recess or recesses preferably has a side or sides parallel to the plane of the partition member of 0.15 to 0.25 inch in length. This represents a larger diameter recess and a larger intersecting radial slit within it, than has been previously used, for example, on the prior art catheter sheath introducer valves sold by the Cordis Corporation within the scope of the above cited U.S. Patents.

Apart from that, it can be seen that a significant difference of the partition of this invention from the respective Hillstead patents is that: in Hillstead Patent No. 4,798,594 no recesses at all are used. In Hillstead U.S. Pat. No. 4,895,565, a pair of opposed recesses are used which are not of rectangular cross section, but, rather, are of arced cross section.

It has been found that significant advantages are achieved by the partition valves of this invention over the prior art valves of Hillstead of comparable dimensions, when the new geometry of this invention is used. Specifically, the thickness of the partition throughout the recesses in accordance with this invention may be substantially constant, in view of the rectangular configuration. Thus, at the center of the partition, in the area of the slit, the partition may be a bit thicker than is optimum for the prior art partition at the same location. A greater thickness improves the sealing of the partition of this invention. However, near the edges of the recess or recesses, the thickness of the partition is substantially constant relative to the center of the partition in this invention. In the prior art partitions with arced recesses, the thickness of the partition near the edge of the recesses is substantially thicker than at the center, resulting in increased friction. Thus, the partition of this invention exhibits relatively decreased frictional characteristics coupled with the improved sealing characteristics, when compared with the partitions of the prior art.

Thus, while the partitions disclosed in the cited patents are believed to be the best prior art design for slit partition valves of this type, the valves of this invention provide a substantial and measurable functional improvement.

Preferably, the elastomeric material used in the partition member and through which the slit is defined comprises a silicone rubber, although it believed that other elastomers exhibiting equivalent properties may be used. Preferably, the slit-defining elastomeric material of the partition has an elongation to break of nine hundred to fifteen hundred percent as measured by the usual and conventional ASTM D412.

In the prior art slit partition hemostasis valve sold by the Cordis Corporation, a silicone rubber partition is used having a maximum elongation of about 750 percent as measured in similar manner. It has been found that the higher elongations used in this invention help to provide improved sealing characteristics over the prior art structures.

Also it is preferred for the elastomeric material to have a tensile strength of at least 11.5 megapascals, up to generally a practical maximum of about 15 megapascals, as measured by the same ASTM D412.

In the prior art slit partition valve sold by the Cordis Corporation and mentioned above, the tensile strength of the material of the elastomer partition is about 10.9 megapascals, which is of course significantly below the tensile strength of the elastomer materials used in this invention. This also contributes to the advantages of this invention as described above.

It is also preferred for the elastomeric material used herein to have a Shore A durometer of 45 to 70 as measured by ASTMD 2240. The durometer of the prior Cordis slit partition hemostasis valve is about 40. These higher durometers used herein result in less frictional resistance exhibited by the valve.

Specifically, silicone elastomer materials which are preferred for use are available from the Dow Corning Corporation of Midland, Mich. under the name Silastic Q7-47-35, 50 or 65 medical grade ETR elastomer. The latter two digit numbers refer to the Shore A durometers of the materials.

The preferred tear strength of the elastomers used is at least 150 pounds/inch, as determined by ASTM D624, Die B. Preferably, the tear strength is at least 180 pounds/inch, with no critical maximum tear strength.

It is also preferred for at least one of the faces of the elastomeric partition, i.e. that face which rubs against the catheter or the like passing through it, to be coated with a silicone oil having a viscosity of 350 to 5000 cs. In the prior art Cordis product, Dow Corning 360 medical grade dimethylpolysiloxane oil was used, with the oil having a viscosity of 12,500 cs. It has been found that a reduction in frictional resistance can be achieved by reducing the viscosity of the silicone oil used to the above range, and applying it to the partition valve face. The silicone oil may comprise other silicones than dimethylpolysiloxane if desired, for example phenylmethylpolysiloxane, copolymers with dimethylpolysiloxane, or polymers or copolymers having 3, 3, 3-trifluoropropylmethylsiloxane units.

Thus, by this invention, a partition valve is provided having significant distinctions from the valves of the prior art, and which are capable of exhibiting significant improvements in both sealing and friction reduction, with a substantially reduced risk of tearing of the valve during use.

DESCRIPTION OF SPECIFIC EMBODIMENTS

Figure 1:
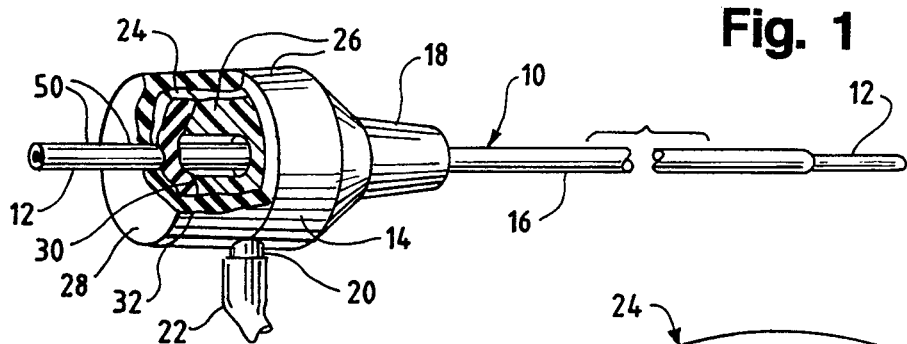
FIG. 1 is a perspective view, with a portion cut away, of a catheter introducer sheath which carries the hemostasis valve of this invention.

Referring to FIGS. 1 through 5, FIG. 1 shows a catheter sheath introducer 10, adapted to receive an inner catheter 12 as shown for inserting into the vascular system of a patient. Catheter sheath introducer 10 is used to introduce a catheter into a blood vessel while preventing blood backflow along the outside surface of the catheter during procedures in which a catheter is inserted into the vessel.

Catheter sheath introducer 10 defines outer tubular housing 14 which carries cannula portion 16 of catheter sheath introducer 10, positioned in attached, telescoping relation with tubular protrusion 18 of the housing. Side port 20 may be of conventional design, being adapted for telescoping connection with plastic tubing 22, for providing a saline solution for flushing the interior of housing 14 and tubing extension 16.

Housing 14 carries a self-sealing, penetrable barrier: as elastomeric partition valve member 24, which is made in accordance with this invention, preferably of silicone rubber as previously described. Apart from the new and improved design of partition valve member 24, the catheter sheath introducer of FIG. 1 may be identical to those of the prior art.

Housing 14 may comprise casing portions 26, 28 which are sealed together in telescoping relation, and which peripherally capture penetrable barrier 24 between them as shown. Barrier 24 may be held with good sealing in those preferred cases as shown in which the peripheral portion of barrier or partition 24 is thicker than the inner, central portion. However, the elastomeric partition of this invention may alternatively be a flat disk or other shape without any recesses as described herein, making use of the elastomer materials having properties as described herein to achieve advantages in accordance with this invention.

Alternatively, casing portion 28 may be a screw cap, for adjustable, compressive retention of elastomeric barrier 24. Annular ribs 30, 32 may be provided in each housing portion to provide more positive capture of the elastomeric portion 24.

Referring to FIGS. 2 through 5, details of the slit design in partition member 24 are disclosed. Specifically, the cross-sectional shape of slit 40 is shown to be of the shape of three intersecting, substantially equiangularly spaced radii, spaced about an origin line 48 by about 120° and defined on both major faces 50, 52. Alternatively, with four equiangularly spaced radii, the included angle between each radius may be 90°. Six spaced radii may define included angles of 60°. Two equiangularly spaced radii define and include an angle with each other of 180°, and thus define a single, straight line, for a simplified version of the radial arrangement.

Figure 3:
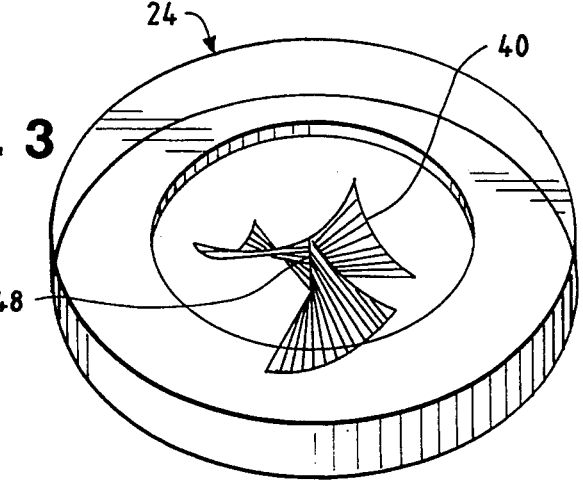
FIG. 3 is a perspective view of the elastomeric partition member of FIG. 2 showing the slit pattern.
Figure 2:
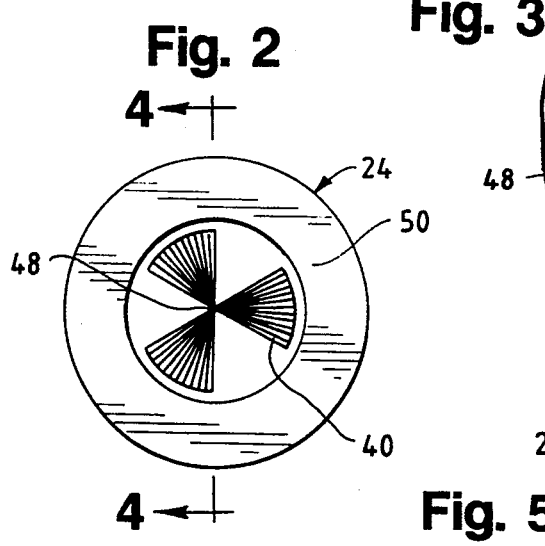
FIG. 2 is an enlarged, plan view of the elastomeric partition member of FIG. 1, showing a preferred slit pattern in the partition member.
Figure 5:
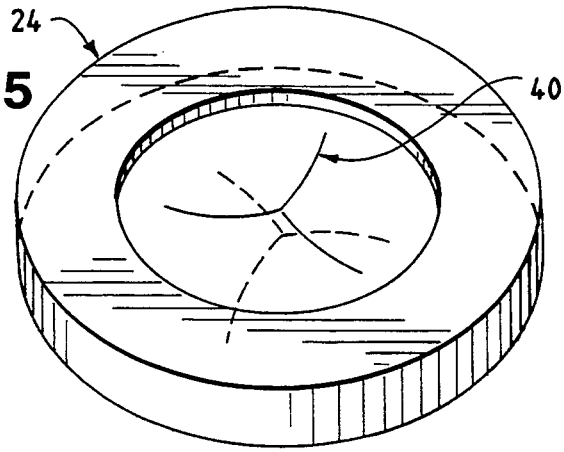
FIG. 5 is a perspective view of the elastomeric partition member of FIG. 2.
Figure 4:
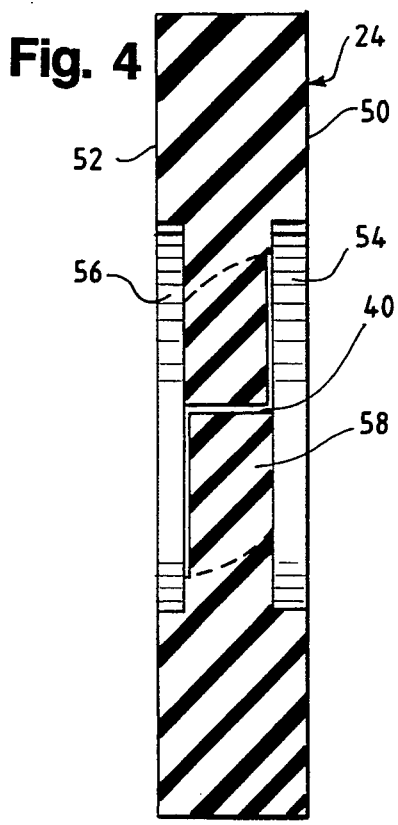
FIG. 4 is an enlarged, transverse, sectional view taken along line 4—4 of FIG. 2.

As radial slit 40 extends through partition 24, it preferably rotates to form a plurality of helical planes, and emerges from the other side 52 of the partition to define spaced radii that define an angle to their original position on face 50, as shown in FIGS. 3–5, and as described in further detail in the patents discussed above.

The radial slits in FIGS. 3 and 5 are shown to have a slight curve to them. Also, they may be entirely straight and perfectly radial. The slight arcs in the otherwise radial lines on the major faces of the partition valve may result even though they were initially cut straight, due to compressive forces in the elastomeric valve after it is installed in a housing and also the torque of the cutting tool during the manufacturing process. It follows that the original, cut lines on the major faces may be originally curved, if desired, which does not preclude them from being effectively radial.

In one embodiment accordance with this invention, partition valve 24 may define a tri-radial, spiral cut as shown in FIGS. 2 through 5, being made of Dow Corning Q7-4765 silicone elastomer. Such a partition may be circular, with a diameter of 0.31 inch and a maximum thickness of 0.07 inch as shown. Partition 24 defines a pair of opposed, circular recesses 54, 56 of rectangular cross-section as specifically shown in FIG. 4, i.e. walls that are perpendicular to the diameter of circular partition valve disk 24. The thickness of partition 24 at recesses 54, 56 may be 0.05 inch, while the diameter of each of circular recesses 54, 56, shown in registry with each other, may each be 0.15 inch.

The Dow Corning Q7-4765 silicone elastomer from which partition 24 is made may have an elongation of 900 percent and a Shore A durometer of 65. The tensile strength of this material is 200–230lb/in. The surface of recess 56, which faces the proximal end of catheter sheath introducer 10, may be coated with a dimethylpolysiloxane fluid having a viscosity of 1,000 cs.

The above embodiment of this invention exhibits significant improvements in the reduction of back leakage and the reduction of friction to advancing catheters over any catheter sheath introducer valve known to the applicants.

As a second embodiment, a partition valve similar to the above may be provided except that the thickness of the partition at area 58 may be 0.04 inch, and the diameters of circular recesses 54, 56 may be 0.170 inch. Similar excellent improvements of operation may be achieved by this embodiment.

As a third embodiment, the partition as described in the first embodiment may be modified only by the use of Dow Corning Q7-4750, elastomer with no other changes, to provide a durometer of 50. Similar excellent results are achieved.

Other embodiments of partition 24 are as disclosed in tabular form below. In each of the embodiment disclosures below, the partition is of the design specifically shown in FIG. 4 with two opposed rectangular recesses 54, 56 and a spiral-cut slit 40 of a type similar to the disclosure of FIGS. 3–5. Dimension A is the diameter of the partition which is a disk with a circular periphery. Dimension B is the peripheral thickness of the partition. Dimension C is the thickness of the partition between the two recesses. Dimension D is the diameter of the recesses, the recesses being circular. The durometer is Shore A durometer as described above. The elongation is in percentage and determined as described above. All of the embodiments are treated with 1,000 cs. dimethylpolysiloxane fluid. The elastomer type is Dow Corning Q7-4735, 4750, or 4765, the last two digits thereof corresponding to the durometer. The tear strength of each of the elastomers used is 200–230 pounds per inch.

Varying numbers of radial slits are provided in the embodiments below, all connecting at an origin, namely three, four and six radial slits with equiangular distribution. Each entry below gives the number of slits.

4. A. 0.310
   B. 0.070
   C. 0.030
   D. 0.190
   Durometer 35
   Elongation 1,200
   No. of Slits 3
5. A. 0.310
   B. 0.070
   C. 0.040
   D. 0.170
   Durometer 35
   Elongation 1,200
   No. of Slits 3
6. A. 0.310
   B. 0.070
   C. 0.050
   D. 0.150
   Durometer 35
   Elongation 1,200
   No. of Slits 3
7. A. 0.310
   B. 0.070
   C. 0.030
   D. 0.190
   Durometer 50
   Elongation 900
   No. of Slits 3
8. A. 0.310
   B. 0.070
   C. 0.040
   D. 0.170
   Durometer 50
   Elongation 900
   No. of Slits 3
9. A. 0.310
   B. 0.070
   C. 0.030
   D. 0.190
   Durometer 65
   Elongation 900
   No. of Slits 3
10. A. 0.310
    B. 0.070
    C. 0.030
    D. 0.190
    Durometer 35
    Elongation 1,200
    No. of Slits 4
11. A. 0.310
    B. 0.070
    C. 0.040
    D. 0.170
    Durometer 35
    Elongation 1,200
    No. of Slits 4
12. A. 0.310
    B. 0.070
    C. 0.050
    D. 0.150
    Durometer 35
    Elongation 1,200
    No. of Slits 4
13. A. 0.310
    B. 0.070
    C. 0.030
    D. 0.190
    Durometer 50
    Elongation 900
    No. of Slits 4
14. A. 0.310
    B. 0.070
    C. 0.040
    C. 0.170
    Durometer 50
    Elongation 900
    No. of Slits 4
15. A. 0.310
    B. 0.070
    C. 0.050
    D. 0.150
    Durometer 50
    Elongation 900
    No. of Slits 4
16. A. 0.310
    B. 0.070
    C. 0.030
    D. 0.190
    Durometer 65
    Elongation 900
    No. of Slits 4
17. A. 0.310
    B. 0.070
    C. 0.040
    D. 0.170
    Durometer 65
    Elongation 900
    No. of Slits 4
18. A. 0.310

-continued

| | |
|---|---|
| | B. 0.070 |
| | C. 0.050 |
| | D. 0.150 |
| | Durometer 65 |
| | Elongation 900 |
| | No. of Slits 4 |
| 19. | A. 0.310 |
| | B. 0.070 |
| | C. 0.030 |
| | D. 0.190 |
| | Durometer 35 |
| | Elongation 1,200 |
| | No. of Slits 6 |
| 20. | A. 0.310 |
| | B. 0.070 |
| | C. 0.040 |
| | D. 0.170 |
| | Durometer 35 |
| | Elongation No. 1,200 |
| | No. of Slits 6 |
| 21. | A. 0.310 |
| | B. 0.070 |
| | C. 0.050 |
| | D. 0.150 |
| | Durometer 35 |
| | Elongation 1,200 |
| | No. of Slits 6 |
| 22. | A. 0.310 |
| | B. 0.070 |
| | C. 0.030 |
| | D. 0.190 |
| | Durometer 50 |
| | Elongation 900 |
| | No. of Slits 6 |
| 23. | A. 0.310 |
| | B. 0.070 |
| | C. 0.040 |
| | D. 0.170 |
| | Durometer 50 |
| | Elongation 900 |
| | No. of Slits 6 |
| 24. | A. 0.310 |
| | B. 0.070 |
| | C. 0.050 |
| | D. 0.150 |
| | Durometer 50 |
| | Elongation 900 |
| | No. of Slits 6 |
| 25. | A. 0.310 |
| | B. 0.070 |
| | C. 0.030 |
| | D. 0.190 |
| | Durometer 65 |
| | Elongation 900 |
| | No. of Slits 6 |
| 26. | A. 0.310 |
| | B. 0.070 |
| | C. 0.040 |
| | D. 0.170 |
| | Durometer 65 |
| | Elongation 900 |
| | No. of Slits 6 |
| 27. | A. 0.310 |
| | B. 0.070 |
| | C. 0.050 |
| | D. 0.150 |
| | Durometer 65 |
| | Elongation 900 |
| | No. of Slits 6 |

Figure 6:
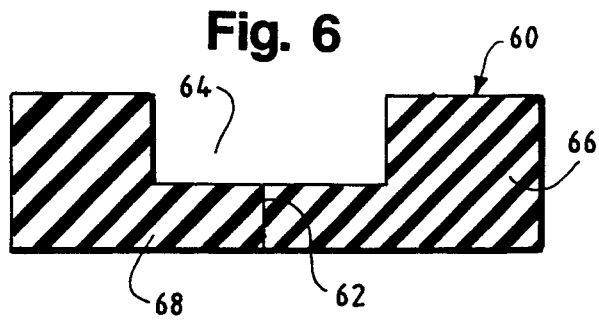
FIG. 6 is a sectional view, similar to that of FIG. 4, of another embodiment of the elastomeric partition member of this invention.

Referring to FIG. 6, another embodiment of an elastomeric partition member 60 is disclosed which may have a slit 62 similar to that which is previously disclosed, or any other desired slit design. In this embodiment, partition 60 defines a single recess 64 which can serve the function of both of the recesses of the prior design of this application, to provide a partition member having a thicker, peripheral portion 66 and a thinner, central portion 68, to achieve the advantages of this invention in equivalent manner. The dimensions and materials discussed above may also be used with this embodiment.

The above has been offered for illustrative purposes only, and is not intended to limit the scope of the invention of this application, which is defined in the claims below.

That which is claimed is:

1. A catheter which comprises a tubular catheter body having a proximal and a distal end, a housing carried on said proximal end, and an elastomeric valve partition member having a first face and a second, opposed face secured in said housing, both of said faces defining a recess of substantially rectangular cross section to reduce the central thickness of said partition member, said rectangular cross section each having a first side parallel to the plane of said partition member which is of greater length than the sides of said rectangular cross section adjacent thereto, and a slit extending between said first and second faces within said recesses, in which said elastomeric partition member comprises a slit-defining elastomeric material which has an elongation of 900 to 1500 percent, whereby elongated members may extend through said partition member and catheter body with sealing at said partition member.

2. The catheter of claim 1 in which the elastomeric material of said partition member has a tensile strength of at least 11.5 megapascals.

3. The catheter of claim 1 in which the elastomeric material of said partition member has a Shore 'A' durometer of 45 to 70.

4. The catheter of claim 1 in which the elastomeric material of said partition member is silicone rubber.

5. The catheter of claim 1 in which the central thickness of said partition member is 0.035 to 0.055 inch.

6. The catheter of claim 1 in which at least one of said faces is coated with a silicone oil having a viscosity of 350 to 5000 cs.

7. The catheter of claim 1 in which said slit defines at each of said faces a plurality of lines extending generally radially from an origin, said lines occupying a circular area having a diameter of at least 0.125 inch and no more than 0.25 inch.

8. The catheter of claim 1 in which the central thickness of said partition member is 0.030 to 0.055 inch, and said rectangular cross section has sides parallel to the plane of said partition member which are 0.15 to 0.2 inch in length.

9. The catheter of claim 1 in which said elastomeric material has a tear of at least 150 pound/inch.

10. A catheter which comprises a tubular catheter body having a proximal and a distal end, a housing carried on said proximal end, and an elastomeric valve partition member having a first face and a second, opposed face secured in said housing, said partition member defining a slit between said faces, said partition member comprising a slit-defining elastomeric material having an elongation of 900 to 1500 percent, whereby elongated members may extend through said partition member and catheter body with sealing at said partition member.

11. The catheter of claim 10 in which said elastomeric material has a tensile strength of at least 11.5 megapascals.

12. The catheter of claim 10 in which at least one of said faces defines a recess of substantially rectangular cross section, the thickness of said partition member in said recess being 0.030 to 0.055 inch.

13. The catheter of claim 10 in which said elastomeric material has a Shore 'A' durometer of 45 to 70.

14. The catheter of claim 10 in which said elastomeric material is silicone rubber.

15. The catheter of claim 10 in which the central thickness of said partition member is 0.030 to 0.055 inch.

16. The catheter of claim 10 in which said elastomeric material has a tear strength of at least 150 pound/inch.

17. The catheter of claim 10 in which at least one of said faces is coated with a silicone oil having a viscosity of 350 to 5000 cs.

18. The catheter of claim 10 in which said slit defines at each of said faces a plurality of lines extending generally radially from an origin, said lines occupying a circular area having a diameter of at least 0.125 inch and no more than 0.25 inch.

19. A catheter which comprises a tubular catheter body having a proximal and a distal end, a housing carried on said proximal end, and an elastomeric valve partition member having a first face and a second, opposed face adapted for securement in a housing, at least one of said faces defining a recess of substantially rectangular cross section to reduce the thickness of said partition at said recess to 0.030 to 0.055 inch, and a slit extending between said first and second faces at said recess, in which said elastomeric partition member comprises a slit-defining elastomeric material having a tensile strength of at least 11.5 megapascals and an elongation of 900 to 1500 percent, whereby elongated members may extend through said partition member and catheter body with sealing at said partition member.

20. The catheter of claim 19 in which said rectangular cross-section has a side parallel to the plane of said partition member which is 0.15 to 0.25 inch in length.

21. The catheter of claim 20 in which the shape of said recess is circular.

22. The catheter of claim 19 in which said elastomeric material has a tear of at least 150 pound/inch.

23. A catheter which comprises a tubular catheter body having a proximal and a distal end, a housing carried on said proximal end, and an elastomeric valve partition member having a first face and a second, opposed face secured in said housing, said partition member defining a slit between said faces, said partition member comprising a slit-defining elastomeric material having an elongation of 900 to 1,500 percent, and a tensile strength of at least 11.5 to 15 megapascals, said slit comprising a first line on said first face and a second line on said second face, said first line and said second line having a similar configuration but being in non-alignment with each other, with a generally helical slit section extending between said first line and said second line through said partition member, whereby elongated members may extend through said partition member and catheter body with sealing at said partition member.

24. The catheter of claim 23 in which said elastomeric material has a tear strength of at least 150.

25. The catheter of claim 24 in which said elastomeric material has a tear strength of at least 180.

26. The catheter of claim 24 in which said elastomeric material has a Shore 'A' durometer of 45 to 70.

27. The catheter of claim 26 in which the central thickness of said partition member is 0.035 to 0.055 inch.

28. The catheter of claim 27 in which at least one of said faces defines a recess of substantially rectangular cross section, said rectangular cross section having a side parallel to the plane of said partition member which is 0.15 to 0.25 inch in length.

29. The catheter of claim 28 in which said slit defines at each of said faces a plurality of lines extending generally radially from an origin, said lines occupying a circular area within said recess having a diameter of at least 0.125 inch and no more than 0.25 inch.

30. The catheter of claim 29 in which at least one of said faces is coated with a silicone oil having a viscosity of 350 to 500 cs., said elastomeric material being silicone rubber.

* * * * *